United States Patent [19]

Bowers et al.

[11] Patent Number: 4,892,562

[45] Date of Patent: Jan. 9, 1990

[54] DIESEL FUEL ADDITIVES AND DIESEL FUELS CONTAINING SOLUBLE PLATINUM GROUP METAL COMPOUNDS AND USE IN DIESEL ENGINES

[75] Inventors: Wayne E. Bowers, Clearwater, Fla.; Barry N. Sprague, West Haven, Conn.

[73] Assignee: Fuel Tech, Inc., Stamford, Conn.

[21] Appl. No.: 897,864

[22] Filed: Aug. 19, 1986

Related U.S. Application Data

[63] Continuation-in-part of Ser. No. 796,428, Nov. 8, 1985, abandoned, which is a continuation-in-part of Ser. No. 677,954, Dec. 4, 1984, abandoned, which is a continuation-in-part of Ser. No. 790,738, Oct. 24, 1985, abandoned.

[51] Int. Cl.$^4$ .............................................. C10L 1/30
[52] U.S. Cl. .......................................... 44/67; 44/56; 44/57; 44/68
[58] Field of Search ....................... 44/57, 67, 68, 56; 260/429 R; 556/136

[56] References Cited

U.S. PATENT DOCUMENTS

| | | | |
|---|---|---|---|
| 2,875,223 | 2/1959 | Pedersen et al. | 44/68 |
| 4,207,078 | 6/1980 | Sweeney et al. | 44/68 |
| 4,242,099 | 12/1980 | Malec | 44/53 |

OTHER PUBLICATIONS

Belluco, Organometallic & Coord. Chem of Platinum, Academic Press, N.Y., pp. 221, 222, 226, 232, 295–297, 441–442, 449, 454 & 455 (1974).
Deganello, Transition Metal Complexes of Cyclic Polyolefins, Academic Press, N.Y., pp. 97–100, 102, 277–278, 281 & 288–291 (1979).
Dickson, Organometallic Chemistry of Rhodium & Iridium, Academic Press, N.Y., pp. 167–169, 178–180, 198–200, 220–226, 248, 258–260, 264, 271 & 277, 1983.
Maitlis, The Organic Chemistry of Palladium, Academic Press, N.Y., pp. 68, 70, 76, 77, 83, 93, 102, 103, 136, 158, 165, 202–204, 228, 242, 249, 257–258 (1971).
Chemical Abstracts 76112565p (1972); 76113355g (1972).
Chemical Abstracts 824403z (1975).
Chemical Abstracts 97110175w (1982) and 97110181v (1982).

*Primary Examiner*—William R. Dixon, Jr.
*Assistant Examiner*—Margaret B. Medley
*Attorney, Agent, or Firm*—St. Onge, Steward, Johnston & Reens

[57] ABSTRACT

The invention provides diesel fuel additive compositions comprising solutions of diesel fuel-soluble platinum group metal compounds in solvents miscible in the fuel, the platinum group metal complex being present in an amount sufficient to supply from 0.01 to 1.0 parts per million of the platinum group metal when added to a predetermined amount of fuel. Fuel compositions and methods employing them are also provided.

18 Claims, No Drawings

DIESEL FUEL ADDITIVES AND DIESEL FUELS CONTAINING SOLUBLE PLATINUM GROUP METAL COMPOUNDS AND USE IN DIESEL ENGINES

RELATED APPLICATIONS

This application is a continuation-in-part of commonly assigned co-pending patent application Serial No. 796,428 filed Nov. 8, 1985 now abandoned, which in turn is a continuation-in-part of prior applications Ser. No. 677,954, filed on 4 Dec. 1984 now abandoned, and Ser. No. 790,738, filed on Oct. 24, 1985 now abandoned, all by Bowers and Sprague, the inventors herein.

DESCRIPTION

1. Technical Field

The present invention relates to improving the performance of internal combustion diesel engines, and, more particularly, to the formulation and use of diesel fuel additives and fuels which burn more efficiently and with reduced noxious emissions.

2. Background Art

Prior investigations involving the use of platinum group metals in internal combustion engines have led to the development of the catalytic converter for emissions reduction in gasoline engines. Reliance upon costly mechanical equipment is less than ideal or desirable and it would be more desirable to accomplish the same result through less costly combustion improvements in terms of better combustion conditions through engine design and fuel additives. Efforts in engine design have provided significant improvements, but the twin objectives of improved operating efficiency and reduced noxious emissions are difficult to achieve simultaneously.

Experience to date with fuel additives has been less successful. For example, in U.S. Pat. Nos. 2,086,775 and 2,151,432, Lyons and McKone disclose adding from 0.001 to 0.085% (i.e., from 10 to 850 parts per million) of an organometallic compound or mixture to a base fuel such as gasoline, benzene, fuel oil, kerosene, or blends to improve various aspects of engine performance. Among the metals disclosed in U.S. 2,086,775 are cobalt, nickel, manganese, iron, copper, uranium, molybdenum, vanadium, zirconium, beryllium, platinum, palladium, chromium, aluminum, thorium and the rare earth metals, such as cerium. Among those disclosed in U.S. 2,151,432 are selenium, antimony, arsenic, bismuth, cadmium, tellurium, thallium, tin, barium, boron, cesium, didymium, lanthanum, potassium, sodium, tantalum, titanium, tungsten and zinc. In both disclosures, the preferred organometallic compounds were beta diketone derivatives and their homologues, such as the metal acetylacetonates, propionylacetonates, formylacetonates, and the like.

The Lyons and McKone disclosures state that concentrations of from 0.001 to 0.04% (i.e., from 10 to 400 parts per million) are not effective to improve combustion efficiency as introduced, but may become so upon prolonged use as catalytically active deposits are built up in the combustion chamber. The disclosure further states that about 0.01% (i.e., 100 ppm) of the organometallic compound is usually sufficient, once the requisite amount of catalytically active deposits has been built up, to perpetuate that amount of deposits by replacement of losses therefrom. U.S. Pat. No. 2,460,780 to Lyons and Dempsey, which relates principally to water-soluble catalysts, confirms this at column 1, lines 11–36. Thus, the levels found effective were of questionable economics and no effectiveness was suggested for lower levels.

In Demonstration 15 in U.S. Pat. No. 2,086,775, palladium acetylacetonate was added to a fuel (not specifically identified, but presumably the leaded 65 octane gasoline employed in Demonstration 1) at a level of 0.002% (20 ppm). The level of palladium is found by calculation to be about 10 ppm. No improvement in combustion was noted until after substantial driving.

The above-noted U.S. Pat. No. 2,460,780 to Lyons and Dempsey relates principally to employing catalysts which are soluble in water or other "internal liquid coolants" such as alcohol, water-soluble glycols or aqueous solutions of these. While catalyst levels based on the weight of metal compounds as low as 0.001% are disclosed, it is stated that for immediate catalytic effect the catalyst compounds for useful effect may be present at a level of at least 1% of the weight of the operating fuel charge. In some Examples, fuel-soluble cobalt, cerium and chromium catalysts are added to the fuel at total catalyst levels of 0.01%. No disclosure is given of fuel-soluble catalysts at levels below 0.01%.

In U.S. Pat. No. 4,295,816, Robinson discloses an elaborate delivery system for introducing water-soluble platinum group metal salts through the air intake of oil burner or gasoline engines to deliver platinum group metal catalysts to the combustion chamber at a level no greater than 9 mg catalyst per kilogram of fuel. The equipment is, unfortunately, mor complicated than would be desired for diesel automotive operations and the water-soluble salts employed, e.g., holides, have disadvantages alone and when dissolved.

In German Offenlegungsschrift 2,500,683, Brantl discloses that a wide variety of catalytic metals may be added to hydrocarbon fuels to reduce nitrogen monoxide and oxidize carbon monoxide at the moment of combustion in internal combustion engines. The disclosure states that organometallic or Grignard compounds of the metals lithium, sodium, lead, beryllium, magnesium, aluminum, gallium, zinc, cadmium, tellurium, selenium, silicon, boron, germanium, antimony and/or tin can be added to the fuel individually or as a mixture. Similarly, the metal complexes of the metals scandium, titanium, vanadium, chromium, manganese, iron, cobalt, nickel, copper, zinc, ruthenium, rhodium, palladium, osmium, iridium, platinum, silver, gold, gallium, molybdenum, lead and mercury, with different ligands, can be added to the fuel individually or as a mixture. For the platinum group metals osmium, iridium, and platinum, broad concentrations of from 0.347 to 3.123 grams per liter of fuel are suggested for the various compositions listed in the disclosure, with the range for particularly favorable results being from 0.868 to 1.735 grams per liter of fuel. Considering the cost of these metals and the compositions containing them, there is a negative incentive for employing them at the high levels stated by the disclosure to be effective. Moreover, the tetramethyl platinum compound is not known to exist.

In U.S. Pat. No. 2,402,427, Miller and Lieber disclose the use of certain diesel-fuel-soluble organic or organometallic compounds as ignition promoters at concentrations of from 0.02 to 3% (i.e., 200 to 30,000 parts per million). No platinum group metal compounds are identified.

Other work done, in which cylinders of a diesel engine were coated with platinum metal, showed reductions in noxious emissions, but the coating wore off in a number of hours.

DISCLOSURE OF INVENTION

The present invention comprises the application of certain platinum group metal compounds which are directly soluble in diesel fuel or solvents for use in diesel engines. The compounds, preferably in combination with a solvent for them which is also miscible in the fuel, are employed at very small, but catalytically-effective levels to provide from about 0.01 to about 1.0 parts of platinum group metal per one million parts of fuel (ppm). For the purposes of this description, all part per million figures are on a weight to volume basis, i.e., mg/liter, and percentages are given by weight, unless otherwise indicated.

According to one its aspects, the invention provides diesel fuel additive compositions comprising a solution of a fuel-soluble platinum group metal compound in a solvent miscible in the fuel, the platinum group metal compound being present in an amount sufficient to supply from 0.01 to 1.0 parts per million of the platinum group metal when added to a predetermined amount of fuel.

Among the preferred platinum group metal compounds are platinum group metal coordination compounds comprising a platinum group metal having a +2 or +4 oxidation state with at least one coordination site in the compound being occupied by a functional group containing at least one unsaturated carbon-to-carbon bond with an olefinic, acetylenic or aromatic pi bond configuration. Especially preferred compounds are those of the general empirical formula:

$$X M^{II} R_2$$

where X is a cyclooctadienyl ligand; M is a platinum group metal; and R is benzyl, phenyl or nitrobenzyl.

According to another aspect of the invention, diesel fuel compositions of improved properties are provided, which comprises diesel fuel and an additive composition dissolved therein, said additive composition comprising a fuel-soluble platinum group metal compound in an amount effective to supply from 0.01 to 1.0 parts of the platinum group metal per million parts of fuel.

According to a further aspect of the present invention, there is provided a method of increasing the utilizable energy of diesel fuel for powering internal combustion engines, comprising admixing with said diesel fuel an additive composition comprising a fuel-soluble platinum group metal compound in an amount effective to supply from 0.01 to 1.0 parts of the platinum group metal per million parts of fuel.

The additive compositions according to the invention improve operating efficiency of diesel internal combustion engines in terms of increased power output per unit of fuel burned and reduce the emissions of particulates and noxious gases such as carbon monoxide and nitrogen monoxide. The additives, when added to diesel fuel and supplied to a diesel engine, are believed to reduce the so-called "delay period", which occurs immediately after injection of the fuel into the combustion chamber is initiated, due to improvement in the shape of the indicator diagram. This reduction in delay between vaporization and emission can explain the improvements noted by the present invention but not suggested by the prior art; however, this theoretical explanation is presented only because it is the best available and there may well be others which even better explain the surprising results noted. The additives provide beneficial results over long periods of continuous use.

Diesel fuels, for the purposes of this description, are defined as fuel oil number 2 petroleum distillates of volatility and cetane number characteristics effective for the purpose of fueling internal combustion diesel engines.

As indicated above, the preferred platinum group metal compounds are coordination compounds. These compounds, especially those coordinated with certain high molecular weight (preferably above 100 daltons) olefinic functional groups, are stable in the presence of moisture. This is extremely important due to the amounts of water present in commercial solvents and diesel fuels.

Few, if any, platinum group metal coordination compounds which are directly soluble in gasoline or diesel fuel are available commercially. Compounds which are available often contain objectionable functional groups containing halogen and phosphorus and, therefore, are less than preferred for many internal combustion applications. Preferably, the compounds according to the present invention will have no phosphorus or have low levels which are free of significant disadvantages. We have discovered that certain platinum group metal compounds are soluble and stable in the fuels and actively catalyze the combustion of diesel fuel in internal combustion engines and reduce noxious emissions when introduced as an integral part of the fuel.

The preferred class of materials used include platinum group metal oxidation states II and IV. Compounds in the lower (II) state of oxidation are preferred due to their function in generating the catalytic effect. A significant feature of the invention is the use of platinum group metal II coordination compounds having at least one coordination site occupied by a functional group containing an unsaturated carbon-to-carbon bond of the olefinic, acetylenic or aromatic pi bond configuration. Preferably, two or more of the coordination sites will be occupied by such functional groups since the stability and solubility in diesel fuel of compounds having such multiple functional groups are improved. While not wishing to be bound to any particular theory, it is believed that such preferred compounds in the lowest possible oxidation state are the most beneficial for producing the desired catalytic effect.

Occupation of one or more coordination sites with the following unsaturated functional groups has been found useful:

1. Benzene and analogous aromatic compounds such as anthracene and naphthalene.
2. Cyclic dienes and homologues such as cyclooctadiene, methyl cyclopentadiene, and cyclohexadiene.
3. Olefins such as nonene, dodecene, and polyisobutenes.
4. Acetylenes such as nonyne and dodecyne.

These unsaturated functional groups, in turn, can be substituted with nonhalogen-substituents such as alkyl, carboxyl, amino, nitro, hydroxyl and alkoxyl groups. Other coordination sites can be directly occupied by such groups.

The general formula for the preferred coordination II compounds is:

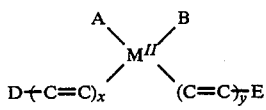

where $M^{II}$ represents the platinum group metal, with a valence of +2, where A, B, D, and E are groups such as alkoxy, carboxyl, etc. described above, where (C=C)x and (C=C)y represent unsaturated functional groups coordinated with the platinum group metal, and where x and y are any integer, typically 1 to 5.

Platinum group metals include platinum, palladium, rhodium, ruthenium, osmium, and iridium. Compounds including platinum, palladium and rhodium, especially platinum in combination with palladium and/or rhodium, are preferred in the practice of this invention.

Fuel additives containing platinum coordination compounds containing platinum in amount of at least 10% of the total platinum group metals are preferred. Particularly good results have been achieved with additives containing a platinum coordination compound in combination with a palladium compound. Preferred weight ratios of platinum to palladium are within the range of from 1:10 to 10:1.

The most preferred platinum group coordination compounds are those represented by the following formula:

$$X\ M^{II}\ R_2$$

wherein X is a cyclooctadienyl ligand, M is a platinum group metal, and R is benzyl, phenyl or nitrobenzyl.

Among other suitable platinum group metal compounds, especially palladium compounds, are the following which include at least one sigma or pi carbon to platinum group metal bond.

(a) 2,2'-bis(N,N-dialkylamino)1,1'-diphenyl metals, as represented by the formula

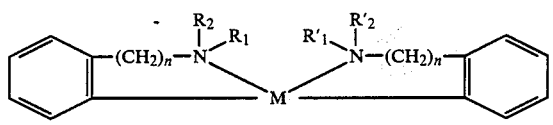

wherein M is a platinum group metal; $R_1$ and $R_2$ are lower alkyl, e.g., from 1 to 10 carbons; and n is an integer from 1 to 5. Representative of this group is 2,2'-bis (N,N-dimethylamino)1,1'-diphenyl palladium. (b) tetrakis (alkoxy carbonyl) metal cycloalkenes, as represented by the formula $$M\ (C_4\ COO\ R_1)_4\ R_2$$

wherein M is a platinum group metal; $R_1$ is a lower alkyl, e.g., from 1 to 5 carbons; and Rz is a cycloalkene having, e.g., from 5 to 8 carbons and from 2 to 4 unsaturations within the ring structure. Representative of this group is tetrakis (methoxy carbonyl) palladia cyclopentadiene. (c) μ-diphenyl acetylene bis ($\eta^5$pentaphenyl cyclopentadiene) di metals as represented by the formula $$(\phi C\ C\phi)\ (C_5\ M)_2$$

wherein M is a platinum group metal and $\phi$ is phenyl. Representative of this group is μ-diphenyl acetylene bis ($\eta^5$-pentaphenyl cyclopentadiene) dipalladium.

(d) dialkyl dipyridyl metals of the formula

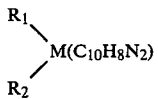

wherein M is a platinum group metal; and $R^1$ and $R^2$ are lower alkyl, e.g., having from 1 to 5 carbons. Representative of this group is diethyl dipyridyl palladium.

(e) bis (π-allyl) metals of the formula $$(R\text{-}C_3\ H_5)_2\ M$$

wherein M is a platinum group metal and R is hydrogen, aryl or alkyl, e.g., one to ten carbons. Representative of this group is bis (phenyl allyl) palladium.

The platinum group metal compound will be added to diesel fuel in an amount effective to improve engine performance in terms of operating efficiency or emissions reduction. Typically, the compound will supply an amount of the metal within the range of from 0.01 to 1.0 parts of the platinum group metal per one million parts of fuel (ppm w/v). A more preferred range is from 0.05 to 0.5 ppm, and most preferably, the platinum group metal will be supplied at a level of from 0.10 to 0.30 ppm on this same basis.

The diesel fuel additive composition will preferably include a solvent which is miscible in the diesel fuel. Certain of the solvents provide enhancements in the effectiveness of the platinum group metal compound and are preferred for this reason. Among the suitable solvents are oxygenated hydrocarbons, such as alcohols, heterocyclic oxygen compounds and ethers. Among the suitable compounds are: 1 to 4 carbon alcohols, e.g., ethanol; tetrahydrofuran; and methyl tertiary butyl ether. Octyl nitrate also functions well in diesel fuel additives.

Where the platinum group metal compound, or one of the several such to be employed, is sensitive to moisture, e.g., metal acetylacetonates, it is important to maintain the moisture content of the solvent and total additive composition sufficiently low that no significant platinum group metal is precipitated. Preferably, additive compositions containing moisture-sensitive components will be substantially free from water.

The solvent will typically be employed at a concentration of up to 5% of the fuel and typically greater than 0.25%. Solvent concentrations of from 0.25 to 2.5% are preferred, and are most preferably 1.0% or less, and in some cases show surprising improvements in additive performance when employed at these levels.

The fuel additive compositions can contain other additives such as detergents, antioxidants and cetane improvers which are known as beneficial, but the use of such is not an essential feature of the invention.

The following examples are presented for the purpose of further illustrating and explaining the present invention and the best mode for carrying it out, and are not to be taken as limiting.

EXAMPLE 1

This example evaluates the performance of a diesel fuel additive according to the invention in reducing light duty diesel emissions and improving fuel economy.

Dibenzyl cyclooctadiene Pt II is used in an additive to diesel fuel supplied to a diesel engine.

Production of dibenzyl cyclooctadiene platinum II is accomplished by slurrying 24.0 grams (0.064 mole) cyclooctadienyl Pt II dichloride in 200 milliliters of xylene. To the resultant mixture is added 0.5 mole benzyl magnesium chloride in diethyl ether (300 milliliters). The Grignard reaction is continued overnight, followed by hydrolysis with saturated ammonium sulfate solution in an ice bath. Following hydrolysis, the mixture is shaken vigorously and the layers are then allowed to separate. The organic phase is collected, dried over anhydrous sodium sulfate, and the residual diethyl ether is removed, leaving a solution of the product in xylene. This product has the structure:

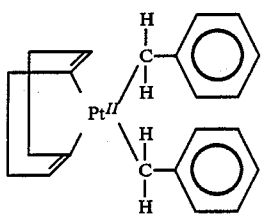

The xylene solution of the platinum compound (0.17% by weight platinum) is admixed with other fuel additive components to provide the formulation set forth in Table 1A below.

TABLE 1A

| Ingredient | Parts by Weight |
| --- | --- |
| Diphenyl Cyclooctadiene Platinum II Coordination Compound | 0.0170 |
| Ethyl Dii-3 Octyl Nitrate | 28.4 |
| Ethyl EDA-2 Detergent | 3.5 |
| Xylene | 2.6 |
| Exxon LOPS Mineral Spirits | 65.5 |

Test Methodology

A 1984 Volvo GLE 760 diesel with five speed transmission and approximately 30,000 miles was selected as a test vehicle to provide data on a newer, but well broken-in, diesel engine.

The vehicle was driven to Scott Environmental Laboratories in Plumsteadville, Pennsylvania and allowed to stabilize for twelve hours prior to chassis dynamometer testing.

Baseline testing was conducted according to U.S. EPA Federal Test Procedures (urban cycle) and Highway Fuel Economy Test procedures. These procedures call for the dynamometer to be loaded to a prescribed setting and the vehicle to be driven through a series of acceleration, shifting, braking and stopping patterns as emissions and fuel economy data are collected. Data are collected over a series of runs and analyzed through a computer software program to arrive at a composite number for emissions and fuel economy performance.

Following baseline testing, the vehicle was treated with additive at the rate of seven ounces per twenty gallons of fuel and released to accumulate on-the-road mileage. The vehicle accumulated 1,600 miles before it was retested. Treatment was maintained during mileage accumulation through the use of pre-packaged additive introduced into the vehicle's fuel tank at each fuel fill-up to give an average concentration of platinum of about 0.15 ppm. Treated fuel testing followed the same procedures as those for baseline testing. The data is summarized in Table 1B.

TABLE 1B

| | Baseline | Treated | % Increase | % Decrease |
| --- | --- | --- | --- | --- |
| Federal Emission Test Data | | | | |
| $CO_2$ | 343.44 | 303.98 | | 11.49 |
| HC | 0.14 | 0.17 | 21.43 | |
| CO | 0.83 | 0.34 | | 59.04 |
| $NO_x$ | 1.00 | 0.48 | | 52.00 |
| Particulate | 0.32 | 0.30 | | 6.25 |
| MPG | 25.69 | 29.07 | 13.16 | |
| Highway Fuel Economy Test Data | | | | |
| $CO_2$ | 231.88 | 199.55 | | 13.94 |
| HC | 0.09 | 0.04 | | 55.56 |
| CO | 0.53 | 0.46 | | 13.21 |
| $NO_x$ | 0.61 | 0.33 | | 45.90 |
| Particulate | — | — | | — |
| MPG | 43.68 | 50.78 | 16.25 | |

EXAMPLE 2

Two diesel passenger automobiles (a Peugeot and a Volkswagen Dasher) were fitted with on-board computers to record trip data and road tested over a 200-mile highway route. In these demonstrations, route and load were held relatively constant, measuring fuel consumption with and without the additive of the invention. The road tests accumulated data for over 7,000 miles driven with untreated fuel and 6,400 miles for fuel treated with the additive detailed in Table 1A to give a platinum metal content of 0.15 ppm. From plots of the regression curves (mpg versus mph) a numerical integration was performed to determine the area under baseline and treated curves. The difference between the two areas was calculated in order to arrive at a percentag figure to describe the increase in mileage due to treatment with the fuel additive.

The results are summarized in Table 2.

TABLE 2

| Peugeot | Linear Regression | 6.55% increase |
| --- | --- | --- |
| | Quadratic Regression | 8.49% increase |
| VW-Dasher | Linear Regression | 6.16% increase |
| | Quadratic Regression | 6.78% increase |

EXAMPLE 3

Trials were conducted over a three-day period to evaluate the performance of the additive detailed in Table 1 A in a Ruston GAPC medium speed diesel engine under closely controlled laboratory conditions. The engine was operated at a constant speed of 750 rpm within a power range of 35 to 85% of maximum continuous rating (MCR).

Baseline fuel tests were performed on the first day, prior to additive introduction on the first and second days. On the first day, baseline fuel flow readings were recorded at power ratios of 35%, 50%, 62.5%, 75% and 85% MCR. Subsequently, additive was introduced in the ratio of one part additive to 250 parts fuel and the power reduced through the above range at hourly intervals. Fuel consumption was recorded at five-minute intervals. At the end of the day's testing, the engine was shut down with additive remaining in the fuel system. The engine had no preconditioning or "seasoning" time on additive.

On the second day, the engine was warmed up and testing began using additive in a concentration of one part to 400. Engine power was progressively increased at hourly intervals through the same points as on the first day, with fuel consumption again recorded at five-minute intervals. An additional baseline (untreated fuel) test was run on the third day.

Analysis of the data collected on the first day presented in Table 3A indicate a reduction in fuel consumption of 3.1% to 5.3% when using the additive. Treated data acquisition progressed from high load (420 kw) to low load (220 kw). Absolute reduction in fuel consumption is noted to improve from no reduction initially (first treated data point) to a 5.3% reduction at the end of the sequence.

Data presented in Table 3B represent a comparison of treated data collected on the second day versus the baseline data of the first day. Percentage reduction in fuel consumption ranged from 3.3% to 4.0% when using the additive. Absolute reduction in fuel consumption is noted to improve from 2.4 kg/hr to 3.3 kg/hr, which follows the trend towards increased time of treatment during the progression from low load operation (275 kw) to high load operation (475 kw) on the second day.

Data collected on the third day (not shown) for untreated operation appear identical to those for treated operation the second day. This is probably the result of a residual effect of additive deposited on cylinder parts and lube oil components during treatment.

TABLE 3A

Comparison of Baseline Fuel Consumption vs. Treated Fuel Consumption at Indicated Loads (First Day Data)

| Power (kw) | Treated Fuel Consumption (kg/hr) | Untreated Fuel Consumption (kg/hr) | Reduction in Fuel Consumption with Additive (kg/hr) | Reduction % |
| --- | --- | --- | --- | --- |
| 420 | 86.8 | 86.8 | — | — |
| 345 | 71.5 | 73.8 | 2.3 | 3.1 |
| 280 | 58.7 | 61.3 | 2.6 | 4.2 |
| 220 | 46.5 | 49.1 | 2.6 | 5.3 |

TABLE 3B

Comparison of Baseline Fuel Consumption vs. Treated Fuel Consumption at Indicated Loads (Second Day Data)

| Power (kw) | Treated Fuel Consumption (kg/hr) | Untreated Fuel Consumption (kg/hr) | Reduction in Fuel Consumption with Additive (kg/hr) | Reduction % |
| --- | --- | --- | --- | --- |
| 275 | 57.6 | 60.0 | 2.4 | 4.0 |
| 347 | 71.2 | 74.2 | 3.0 | 4.0 |
| 410 | 84.0 | 87.1 | 3.1 | 3.6 |
| 475 | 95.9 | 99.2 | 3.3 | 3.3 |

EXAMPLE 4

This test evaluates the effect of the additive detailed in Table 1A on the fuel economy and horsepower output of a commercially-operated, diesel-powered truck tractor.

On the first day of testing, baseline (no additive) chassis dynamometer tests were conducted. The vehicle tested was a tandem tractor powered by a Cummins NHC-250 engine. The vehicle was supplied by an independent owner-operator and was normally used in highway construction hauling. The engine had accumulated 8,000 miles since rebuild.

Following baseline testing and treatment at a rate of one gallon of additive to four hundred gallons of fuel, the vehicle was released to accumulate approximately 1000 miles of over-the-road treated data before being retested on the chassis dynamometer.

During over-the-road mileage accumulation, treatment was maintained by the driver according to a treatment schedule which provided for a 1:400 dosage rate. Product was supplied in one-gallon containers along with a graduated beaker for accurate measurement. Daily record sheets were completed by the driver to record miles driven and fuel and additive consumed.

During dynamometer testing, the tractor was secured to a Clayton water-brake dynamometer and run for four minute intervals at settings of 2100 rpm and full power, 2000 rpm and full power and 1900 rpm and full power. Readings were taken every minute from the dynamometer's gauges, recording the actual rear wheel horsepower. A separate tachometer was installed in the cab. The one in the tractor was found to "bounce". The speed and horsepower balance were maintained at the rear wheels from the cab. Simultaneously, fuel measurements were taken at the same intervals. A thirty gallon drum of fuel was placed on an accurate digital scale and the reduction in the weight of the fuel was recorded. Recirculation was returned to the drum to measure only that fuel consumed. The combined rear wheel horsepower was found to be equal to factory specifications, i.e., 70% of rated 250 horsepower, equal to 175. Prior to testing the engine was checked by the manufacturer to be sure that the fuel flow and fuel pressure agreed with the manufacturer's specifications for the fuel pump.

Two test runs were conducted on each test date to assure the repeatability of results. Each test consisted of three minutes of stabilized run time at each of the three rpm settings with one minute in between to allow for stabilization and transition to the next rpm level.

The averages of three readings for each rpm setting are summarized in Table 4A for untreated and treated data. Table 4A provides a comparison of horsepower (output) versus fuel flow (input) at a given engine rpm for untreated and treated data. Horsepower increases following additive treatment averaged 2.6% to 5.2% improvement over baseline.

Table 4B provides a comparison of actual horsepower increase using the additive versus untreated data. Actual horsepower increases ranged from 4.5 hp to 9.0 hp following additive treatment.

TABLE 4A

Horsepower and Fuel Flow Data at Indicated RPM

| | UNTREATED | | | TREATED | | |
| --- | --- | --- | --- | --- | --- | --- |
| | Run 1 | Run 2 | Avg | Run 1 | Run 2 | Avg |
| (2100) hp | 170 | 174 | 172 | 181 | 181 | 181 |
| Fuel Flow (lb/min) | 1.6 | 1.6 | 1.6 | 1.6 | 1.6 | 1.6 |
| (2000) hp | 172 | 173 | 172.5 | 180 | 180 | 180 |
| Fuel Flow (lb/min) | 1.5 | 1.6 | 1.55 | 1.5 | 1.6 | 1.55 |
| (1900) hp | 173 | 173 | 173 | 177 | 178 | 177.5 |
| Fuel Flow (lb/min) | 1.5 | 1.5 | 1.5 | 1.5 | 1.5 | 1.5 |

TABLE 4B

Actual HP Improvement Resulting from Additive Treatment

| RPM | Untreated (2 run avg) | Treated (2 run avg) | HP Change |
|---|---|---|---|
| 2100 | 172 | 181 | 9.0 |
| 2000 | 172.5 | 180 | 7.5 |
| 1900 | 173 | 177.5 | 4.5 |
| | | Average HP Improvement | 7.0 |

Fuel flow remained nearly constant during the tests, actual horsepower measured by the dynamometer increased for the treated runs. Actual horsepower improvement averaged 7.0 hp for the treated runs over the three rpm settings. This corresponds to a 4.0% increase in horsepower over baseline horsepower.

The dynamometer was not equipped to run treated tests at equivalent baseline horsepower in order to monitor decrease in fuel flow; however, a calculation of brake specific fuel consumption (BSFC) is one means of recording the fact that more work is produced per unit of fuel when using the additive. Therefore, if power requirements were held constant, less fuel would be consumed when using the additive. The data provided in Table 4C represent BSFC, pounds of fuel consumed per horsepower-hour for untreated and treated data. The improvement using additive ranged from 2.5% to 5.0%.

Emissions measurements were not quantified during these tests; however, a reduction in visible smoke emissions was observed when running on treated fuel at start-up, idle and loaded conditions.

TABLE 4C

Brake Specific Fuel Consumption vs. RPM (BSFC in lb per hp-hr)

| | UNTREATED | | | TREATED | | | Improvement |
|---|---|---|---|---|---|---|---|
| RPM | Run 1 | Run 2 | Avg | Run 1 | Run 2 | Avg | |
| 2100 | 0.564 | 0.551 | 0.558 | 0.530 | 0.530 | 0.530 | 5.0% |
| 2000 | 0.523 | 0.554 | 0.539 | 0.500 | 0.533 | 0.517 | 4.1% |
| 1900 | 0.520 | 0.520 | 0.520 | 0.508 | 0.505 | 0.507 | 2.5% |

EXAMPLE 5

This test evaluates the effectiveness of the diesel fuel additive set forth in Table 1A in a high elevation test on large tractors presently used for hauling. Two tractors were selected—a new Kenworth with a 400 horsepower Caterpillar engine (31,000 total miles) and a Kenworth with a 475 horsepower Cummins twin-turbo engine (172,000 total miles).

Testing Method (Over-the-Road)

Baseline data from previous months' records was listed indicating date, miles driven, gallons of fuel used and then miles per gallon was calculated. The two selected vehicles were then tested on a chassis dynamometer for baseline determination (see Testing Method-Chassis Dynamometer). After the dynamometer tests, the tractors were treated with the fuel additive and returned to their commercial routes. The next two months (treated data) were then listed and compared to the original (untreated) baseline data.

Testing Method (Chassis Dynamometer)

Both Kenworth tractors were tested on an Ostradyne Model U130TT chassis dynamometer. The specifications of the unit are horsepower limit 500, torque limit 1500 lb. ft., maximum rear wheel speed was 60 mph.

The tractors were driven onto the dynamometer such that the rear driving wheels of the tractor turned a set of rollers. These rollers are connected to a braking system. The force required on the turning rollers to load the tractor's rear driving wheels is indicated on various meters located on the dynamometer's control panel. The meters consisted of horsepower, torque, speed (calibrated in miles per hour) and also a separate panel with controls to adjust for barometric pressure, humidity, etc.

The test consisted of selecting three basic rpm's in the upper scale of the tractor's capability. The tractor was then fully loaded maintaining the specific rpm and the meters on the dynamometer were recorded every minute for 5 minutes.

Fuel flow was measured by filling a 20 gallon pail with diesel fuel from the tractor's saddle tanks. The 20 gallon pail was placed on an accurate electronic scale. During the 5 minute load tests, minute readings were taken from the scale so an accurate accounting of the fuel usage in pounds of fuel per minute was recorded.

Data Evaluation (Over-the-Road)

The over-the-road data for both tractors is summarized in Tables 5A and 5B. Both tractors showed improvements in excess of 5.6% in MPG while under treatment; with a discernable trend towards continued improvement with time under treatment.

TABLE 5A

Kenworth-Caterpillar

| Baseline | | Treated | |
|---|---|---|---|
| Day | MPG | Day | MPG |
| 1 | 4.13 | 1 | 4.60 |
| 2 | 4.15 | 2. | 4 63 |
| 3 | 4.11 | 3 | 4.86 |
| 4 | 4.20 | 4 | 4.67 |
| 5 | 3.84 | 5 | 4.95 |
| 6 | 4.74 | 6 | 5.02 |
| 7 | 4.15 | | |
| 8 | 4.19 | | |
| N | 8.00 | N | 6.00 |
| AVG | 4.189 | AVG | 4.788 |
| STD | 0.23 | STD | 0.16 |

Improvement with Treatment = 0.599 mpg or 14.300%

TABLE 5B

| Baseline | | Treated | |
|---|---|---|---|
| Day | MPG | Day | MpG |
| 1 | 4.65 | 1 | 4.87 |
| 2 | 4.43 | 2 | 4.64 |
| 3 | 4.75 | 3 | 4.87 |
| | | 4 | 5.20 |
| N | 3.00 | N | 4.00 |
| AVG | 4.610 | AVG | 4.895 |
| STD | 0.134 | STD | 0.200 |

Improvement with Treatment = 0.285 mpg or 6.18%

EXAMPLE 6

A series of dynamometer tests were run employing a series of diesel fuel additives incorporating different platinum group metal compounds, all employed at levels effective to provide about 0.15 ppm of platinum group metal in the fuel. For the tests, a Cummins 250 horsepower, six cylinder diesel engine was mounted on an eddy current dynamometer. Pressure transducers were inserted into the heads of all six cylinders, and an optical shaft encoder was installed to provide a signal for top dead center as well as for every one half degree of crank angle. Pressures were read at each one half degree of crank angle, giving 720 pressure readings per crank shaft revolution. At the end of 60 revolutions, the data was averaged and plotted by computer.

For each plot obtained, three parameters were studied:

1. Peak—The maximum pressure achieved in the cylinder during combustion.

2. Distance—A physical measurement of the horizontal distance between the top dead center axis and the peak of the pressure curve. Shorter distances between top dead center and peak pressure achieved indicate faster propagation of the flame front across the cylinder.

3. MIP—The mean indicated pressure is the average pressure achieved after ignition at top dead center and is an indication of the total work release achieved by combusting the fuel.

In evaluating pressure curves with additive increases in peak pressure and MIP and decreases (shorter) distances were interpreted as a beneficial effect produced by the additive in terms of fuel utilization and useful work derived from combusting the fuel.

The additives were prepared according to the formulation in Table 1A, varying only the platinum group metal as noted in Table 6 below to give 60 PPM metal in the additive and 0.15 PPM metal in the treated diesel fuel.

TABLE 6

A. Platinum group metal compound
Pt coordination compound as in Example 1 - 60 ppm

|  | Peak | Distance | MIP |
|---|---|---|---|
| Baseline | 2.518 | 3.623 | 7.740 |
|  | 2.765 | 3.613 | 9.830 |
|  | 5.283 | 7.236 | 17.57 |
| Treated | 2.507 | 3.620 | 7.620 |
|  | 2.781 | 3.623 | 9.785 |
|  | 5.288 | 7.253 | 17.405 |
| Difference | +0.005 | +0.017 | −0.165 |

B. Platinum Group Metal Compound
Palladium acetyl acetonate - 60 ppm

|  | Peak | Distance | MIP |
|---|---|---|---|
| Baseline | 3.375 | 3.654 | 11.257 |
|  | 3.767 | 3.648 | 14.565 |
|  | 7.142 | 7.302 | 25.822 |
| Treated | 3.386 | 3.644 | 11.23 |
|  | 3.765 | 3.649 | 14.584 |
|  | 7.151 | 7.293 | 25.815 |
| Difference | +0.009 | −0.009 | −0.007 |

C. Platinum Group Metal Compound
Pt coordination compound as in Example 1 - 30 ppm
Palladium acetyl acetonate - 30 ppm

|  | Peak | Distance | MIP |
|---|---|---|---|
| Baseline | 3.104 | 3.619 | 9.850 |
|  | 3.411 | 3.637 | 12.634 |
|  | 6.515 | 7.256 | 22.484 |
| Treated | 3.152 | 3.612 | 9.794 |
|  | 3.508 | 3.602 | 12.750 |
|  | 6.66 | 7.214 | 22.544 |
| Difference | +0.145 | −0.042 | +0.06 |

D. Platinum Group Metal Compound
Pt coordination compound as in Example 1 - 15 ppm
Palladium acetyl acetonate - 45 ppm

|  | Peak | Distance | MIP |
|---|---|---|---|
| Baseline | 3.079 | 3.632 | 10.658 |
|  | 3.342 | 3.598 | 11.776 |
|  | 6.421 | 7.23 | 22.434 |

TABLE 6-continued

|  |  |  |  |
|---|---|---|---|
| Treated | 3.481 | 3.549 | 11.550 |
|  | 3.319 | 3.599 | 12.339 |
|  | 6.800 | 7.148 | 23.889 |
| Difference | +0.379 | −0.082 | +1.455 |

The above description is for the purpose of teaching the person of ordinary skill in the art how to practice the present invention and is not intended to detail all those obvious modifications and variations of it which will become apparent to the skilled worker upon reading the description. It is intended, however, that all such obvious modifications and variations be included within the scope of the present invention which is defined by the following claims.

We claim:

1. A method of reducing emissions from or increasing the utilizable energy of diesel fuel for powering internal combustion engines, comprising admixing with diesel fuel a fuel soluble organo-metallic fuel additive composition in an amount effective to supply from 0.01 to 1.0 parts per million of platinum per part of fuel, said composition comprising a compound having the general formula $$XPtR_1R_2$$

wherein X is a ligand containing at least one unsaturated carbon-to-carbon bond with an olefinic, acetylenic or aromatic pi bond configuration and $R_1$ and $R2$ are, independently, benzyl, phenyl, nitrobenzyl or alkyl having from 1–10 carbons.

2. The method of claim 1 wherein X is a dipyridyl or cyclooctadienyl ligand.

3. The method of claim 1 wherein $R_1$ and $R_2$ are both methyl, phenyl or benzyl.

4. The method of claim 1 wherein said fuel additive composition further comprises a fuel-soluble solvent for said platinum compound.

5. The method of claim 4 wherein said platinum and said solvent are present in amounts sufficient to supply oxygen and metal at a weight ratio of from 1,000:1 to 100,000:1.

6. The method of claim 5 wherein said solvent is octyl nitrate and is employed at a level of from 0.25 to about 5 percent by weight of the fuel.

7. The method of claim 6 wherein said octyl nitrate is employed at a level up to about 1 percent of said composition and said platinum is present at a level of from 0.05 to 0.5 parts per million parts fuel.

8. The method of claim 4 wherein said solvent comprises octyl nitrate, ethanol, tetrahydrofuran, methyl tertiary butyl ether, or combinations of these.

9. The method of claim 8 wherein $R_1$ and $R_2$ each comprise benzyl and said solvent comprises octyl nitrate.

10. The method of claim 8 wherein $R_1$ and $R_2$ each comprise nitrobenzyl and said solvent comprises octyl nitrate.

11. The method of claim 8 wherein said solvent comprises octyl nitrate.

12. A method of increasing the utilizable energy of diesel fuel for powering internal combustion engines, comprising admixing with diesel fuel a fuel soluble organo-metallic fuel additive composition in an amount effective to supply from 0.01 to 1.0 parts per million of platinum group metal per part of fuel, said composition comprising compounds selected from the group consisting of 2,2'- bis (N, N-dialkylamino) 1,1'-diphenyl metals of the general formula

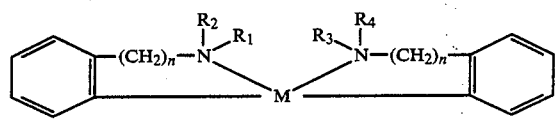

wherein M is platinum, palladium, rhodium or iridium; $R_1$–$R_4$ are, independently, alkyl having from 1–10 carbons; and n is an integer from 1–5; tetrakis (alkoxy carbonyl) metal cycloalkenes of the general formula $R_2MC_4(COOR_1)_4$ wherein M is platinum, palladium, rhodium or iridium; $R_1$ is alkyl having from 1–5 carbons; and $R_2$ is cycloalkene having from 5–8 carbons and from 2–4 unsaturations in the ring structure; bis(cyclopentadiene) acetylene dipalladium compounds of the general formula $(\phi C\ C\phi)(C_5\phi_5)_2Pd_2$ wherein $\phi$ is phenyl; dialkyl dipyridyl metals of the formula $R_1R_2M(C_{10}H_8N_2)$ wherein $R_1$ and $R_2$ are alkyl having from 1–10 carbons; and M is platinum, palladium, rhodium or iridium; and bis ($\pi$-allyl) metals of the general formula $(R-C_3H_4)_2M$ wherein M is platinum, palladium, iridium and rhodium; and R is hydrogen, aryl or alkyl having from 1–10 carbons.

13. The method of claim 12 wherein said compound is selected from the group consisting of 2,2'-bis (N,N-dimethylamino) 1,1'-diphenyl palladium; tetrakis (methoxy carbonyl) palladia cyclopentadiene; $\mu$-diphenyl acetylene bis ($\eta^5$-pentaphenyl cyclopentadiene) dipalladium; and bis (phenyl allyl) palladium.

14. The method of claim 12 wherein said fuel additive composition further comprises a fuel-soluble solvent for said metal compound.

15. The method of claim 14 wherein said metal and said solvent are present in amounts sufficient to supply oxygen and metal at a weight ratio of from 1,000:1 to 100,000:1.

16. The method of claim 15 wherein said solvent is octyl nitrate and is employed at a level of from 0.25 to about 5 percent of the weight of the fuel.

17. The method of claim wherein said octyl nitrate is employed at a level up to about 1 percent of said composition and said metal is present at a level of from 0.05 to 0.5 parts per million parts fuel.

18. The method of claim 14 wherein said solvent comprises octyl nitrate, ethanol, tetrahydrofuran, methyl tertiary butyl ether, or combinations of these.

* * * * *